United States Patent [19]

Shamshoum et al.

[11] Patent Number: 5,210,356

[45] Date of Patent: May 11, 1993

[54] TOLUENE DISPROPORTIONATION EMPLOYING MODIFIED OMEGA ZEOLITE CATALYST

[75] Inventors: Edwar S. Shamshoum; Ashim K. Ghosh, both of Houston; Thomas R. Schuler, Galena Park, all of Tex.

[73] Assignee: Fina Technology, Inc., Dallas, Tex.

[21] Appl. No.: 808,126

[22] Filed: Dec. 16, 1991

[51] Int. Cl.⁵ .............................................. C07C 5/52
[52] U.S. Cl. .................................... 585/475; 585/467
[58] Field of Search ................................ 585/467, 475

[56] References Cited

U.S. PATENT DOCUMENTS

| | | | |
|---|---|---|---|
| 4,241,036 | 12/1980 | Flanigen et al. | 423/328 |
| 4,245,130 | 1/1981 | Jones et al. | 585/481 |
| 4,724,067 | 2/1988 | Raatz et al. | 208/120 |
| 5,030,432 | 7/1991 | Occelli | 423/328 |

Primary Examiner—Asok Pal
Assistant Examiner—P. Achutamurthy
Attorney, Agent, or Firm—M. Norwood Cheairs; Michael J. Caddell; Betty M. Ellsworth

[57] ABSTRACT

The present invention relates to a stable, highly active and selective modified omega zeolite, and its preparation and use in toluene disproportionation.

14 Claims, 2 Drawing Sheets

TOLUENE DISPROPORTIONATION EMPLOYING MODIFIED OMEGA ZEOLITE CATALYST

BACKGROUND OF THE INVENTION

1. Field of the Invention

This invention relates to the disproportionation of alkylaromatic feedstreams and, more particularly, to the disproportionation of toluene containing feedstocks employing a metal-promoted, steam-modified omega zeolite catalyst.

2. Description of the Related Art

The disproportionation of toluene involves a well-known, catalyzed transalkylation reaction in which toluene is converted to benzene and xylene in accordance with the following reaction:

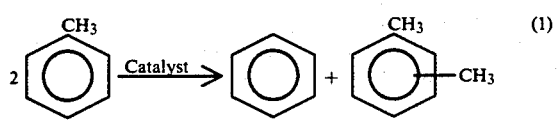

Reaction (1) is mildly exothermic. Crystalline aluminosilicates, or zeolites, are well-known in the art and have found extensive application as hydrocarbon catalysts. While many zeolites occur naturally, more than 40 species of synthetic crystalline zeolites are known to have been prepared within the past decade. These synthetic compositions are distinguishable from each other and from the naturally occurring zeolites on the basis of factors such as composition, crystalline structure, adsorption properties and, perhaps most importantly, characteristic x-ray powder diffraction pattern. Zeolites are of an ordered crystalline structure comprising "cages" or cavities occupied by large ions and water molecules, both of which have considerable freedom of movement, permitting ion exchange and reversible dehydration. Access to these cavities or "channels" is gained by way of orifices within the crystalline lattice. These openings limit the size and shape of molecules that can be adsorbed. A separation of mixtures of molecules based upon molecular dimensions, whereby certain molecules are adsorbed by the zeolite while the entry of others is prevented, is therefore possible. It is this characteristic property of many crystalline zeolites that has led to their designation as "molecular sieves." For a general discussion of zeolite catalysts, reference is made to Kirk-Othmer, Encyclopedia of Chemical Technology, 3rd Edition, 1981 under the heading "Molecular Sieves", Vol. 15, pages 638-643.

In addition to molecular size and shape, however, other factors may also influence the selective adsorption of certain foreign molecules by molecular sieves. Among these factors are: the polarizability and polarity of the adsorbate molecules; the degree of unsaturation of organic adsorbates; the size and polarizing power of the interstitial cation; the presence of adsorbate molecules within the crystalline lattice (interstitial spaces); and the degree of hydration of the zeolite.

In addition to the unique adsorption properties of zeolite molecular sieves, certain of these materials, particularly when chemically modified, are effective catalysts in hydrocarbon conversion processes such as reforming, cracking, isomerization, dehydrogenation and the like. Because the mechanisms involved in these catalytic applications are complex, however, the precise chemical properties of the zeolites which contribute to a particular catalytic activity are not fully understood.

As indicated, many catalytic applications have been discovered for certain zeolites. Among the more widely used and studied zeolite forms are: mordenite, beta and ZSM-5. Lesser known and studied omega zeolite, which is the catalyst employed in the present invention, was first identified by Flanigen, et. al. in U.S. Pat. No. 4,241,036. According to Flanigen, et. al. omega zeolite is not only a distinct species of zeolite molecular sieve but also is a member of a new structural class of zeolites exhibiting a unique and previously unknown framework arrangment of $SiO_2$ and $Al_2O_3$ tetrahedra. While Flanigen, et. al. discloses only the composition of omega zeolite and various procedures by which the composition can be prepared, the inventors did indicate that various cation and decationized forms of zeolite omega could be effective in the hydrocarbon conversion processes commonly referred to as cracking, hydrocracking, isomerization, polymerization, hydrogenation, reforming and paraffin alkylation. This indication notwithstanding, however, and as compared to the aforereferenced and more widely used zeolites, the catalytic properties of omega zeolite are considerably less well known or studied. Low thermal stability has been the reason cited most frequently for the dearth of investigative activity respecting omega zeolite.

According to extant scientific literature, omega zeolite may be destroyed or may undergo a considerable decrease in crystallinity when calcined at temperatures exceeding 600° C. While a number of explanations have been advanced, the reason for the thermal brittleness of omega zeolite remains not well understood. Despite this uncertainty and the variety of postulations, however, recent studies directed toward improving the thermal stability of omega zeolite have been successfully conducted. For example, in Volume 4 of the work entitled "The Synthesis and Thermal Behaviour of Zeolite" (1984) pp. 263-269 by Araya, Abraham, et. al., it is reported that the small quantity roasting of NaTMA omega form in an apparatus of differential thermal analysis leads to a solid which remains crystallized at temperatures up to 800° C. This solid, however, is not dealuminated and retains all initial alkali cations. Earlier work involving the roasting of an $NH_4TMA$ omega compound was reported by Weeks, et. al., in an article appearing in the Journal of the Chemical Society entitled "Thermochemical Properties of Ammonium Exchanged Type Omega Zeolite," Farad Trans 1, 72(1976), 57. Despite some observed thermal stabilization, however, the solid compound failed to demonstrate desirable catalytic activity when tested in hydrocracking and isomerization applications.

In addition to attempts to thermally stabilize the compound, the dealumination of omega zeolite has also been the focus of some investigative activity. U.S. Pat. No. 3,937,791 to Garwood, et. al. discloses the dealumination of various zeolites, including omega zeolite, by Cr (III) salts. This method leads to replacement of the aluminum atoms by chromium atoms. Notwithstanding that the structure is dealuminated, its chromium content is also fatally increased. U.S. Pat. No. 4,297,335 to Lok, et. al. recommends a dealumination technique by treatment with fluorine gas at high temperature. This treatment is applicable to various zeolites but, when applied to omega, it results in degradation of the crystalline structure. European Patent No. 100,544 to Gortsema, et. al. discloses the dealumination of many zeolites, including the omega form, by roasting in the presence of SiCl$_4$ at temperatures lower than 200° C., despite that higher temperatures are known to be required for dealumination in accordance with such technique (Beyer, et. al. Catalysis by Zeolites, (1980) p. 203). The dealumination of omega zeolite by SiCl$_4$ is in fact possible but only at temperatures, for example, above 500° C. as disclosed by J. Klinowski, et. al. JCS, Chem. Commun. 1983, p. 525 and O. Terasaki, et. al. Proc. R. Soc. London (A), 395 (1808), 153-64). Treatment of the omega zeolite by this technique, however, results in a virtually negligible increase in the SiO$_2$ to Al$_2$O$_3$ ratio. Moreover, inasmuch as dealumination by treatment with SiCl$_4$ is applicable to omega zeolite it is essential to note that this technique results in irremediable replacement of the aluminum atoms of the structure with silicon atoms (H. Beyer, et. al. Catalysis by Zeolites, B. Imelik, et. al. editors (1980), p. 203, Elsevier Amsterdam).

Despite the investigative activity described above, the most important advance concerning efforts to both thermally stabilize and dealuminate the omega zeolite form has apparently been made by Raatz, et. al. as disclosed in U.S. Pat. No. 4,724,067. Therein, it is claimed that a practical and useful hydrogen form of omega zeolite can be prepared by a process involving alternating ion exchanges and acid etchings with thermal treatments. Raatz, et. al. further disclose that their process yields a thermally stable, dealuminated omega zeolite in hydrogen form which functions as an active and selective catalyst in cracking and hydrocracking reactions.

While it has been discussed that much investigative work has occurred involving the use of zeolites as catalysts, it is clear that the use of the omega form of the composition remains not fully understood. Moreover, and perhaps due in some measure to the compound's reputation for thermal instability, its known application in the field of alkylaromatic catalysis has been limited to cracking and hydrocracking reactions.

In view of the foregoing, it is clear that a need in the art exists for a means of employing omega zeolite in high level conversion of aromatic hydrocarbons.

SUMMARY OF THE INVENTION

In accordance with the present invention there is provided a method for preparing a highly active, selective and stable metal-promoted and steam modified omega zeolite catalyst for use in the disproportionation of alkylaromatic feedstreams and, more specifically, in the disproportionation of toluene containing feedstocks. The preferred catalyst is of the type designated orthorhombic sodium alumino silicates (zeolites) having a molecular weight in the range of about 2382 to 2886, pore size of its main channel measuring about 7.4 Angstroms and a SiO$_2$/Al$_2$O$_3$ ratio from about 25:1 to 150:1. One particularly advantageous parent catalyst was found to be a zeolite catalyst denominated "Zeolite-Omega" which is sold by Universal Oil Products Company of Des Plaines, Ill. (UOP).

The instant catalyst comprises a metal-promoted zeolite omega, preferably a nickel/omega which characteristically contains about 0.3 to 0.9 wt. % nickel and, preferably, about 0.6 wt. %. While nickel is the preferred metallic hydrogenation agent, the modified omega zeolite catalyst may also be loaded with other Group VIII metals such as Cobalt and Palladium.

The method by which the present zeolite is modified to form the catalyst of the instant invention involves: subjecting the parent zeolite omega composition to an initial ammonium ion exchange after which the resultant dried powder is calcined to effectively remove the catalyst's organic template; subjecting the calcined powder to two successive ammonium ion exchanges; steaming the powder; subjecting the steamed powder to two additional and successive proton ion exchanges under acidic conditions; extruding the powder together with an established amount of alumina binder followed by an additional calcination; and, finally, by employing standard techniques, impregnating the solid extrudate with a desirable amount of a metallic hydrogenation component.

In performing the process of the present invention, an alkylaromatic feedstream, preferably pure toluene, is supplied to a reaction zone and brought into contact with the molecular sieve transalkylation catalyst comprising modified omega zeolite. The modified omega zeolite contains a metallic hydrogenation component, preferably nickel, in a weight percentage amount of about 0.3 to 0.9 and the final catalyst with 20% binder is further characterized by a surface area of more than 420 m$^2$/gram. Hydrogen gas is also supplied to the reaction zone as a cofeed in a molar ratio of about 3.5:1 to 4.5:1. The reaction zone is preferably operated at a temperature of about 250° to 480° C. and at a pressure of about 600 psig, thereby causing the disproportionation of the alkylaromatic feedstock in the presence of the modified omega zeolite/transalkylation catalyst. The resulting transalkylated aromatic products are then recovered from the reaction zone.

A preferred application of the present invention involves the transalkylation of toluene to produce benzene and xylene(s) in the presence of the aforedescribed modified omega zeolite catalyst. The process is performed at transalkylation conditions under which the alkylaromatic feed material is at least 48% converted and relative production of benzene equals or exceeds 40 weight percent.

DESCRIPTION OF THE PREFERRED EMBODIMENTS

Figure 1:
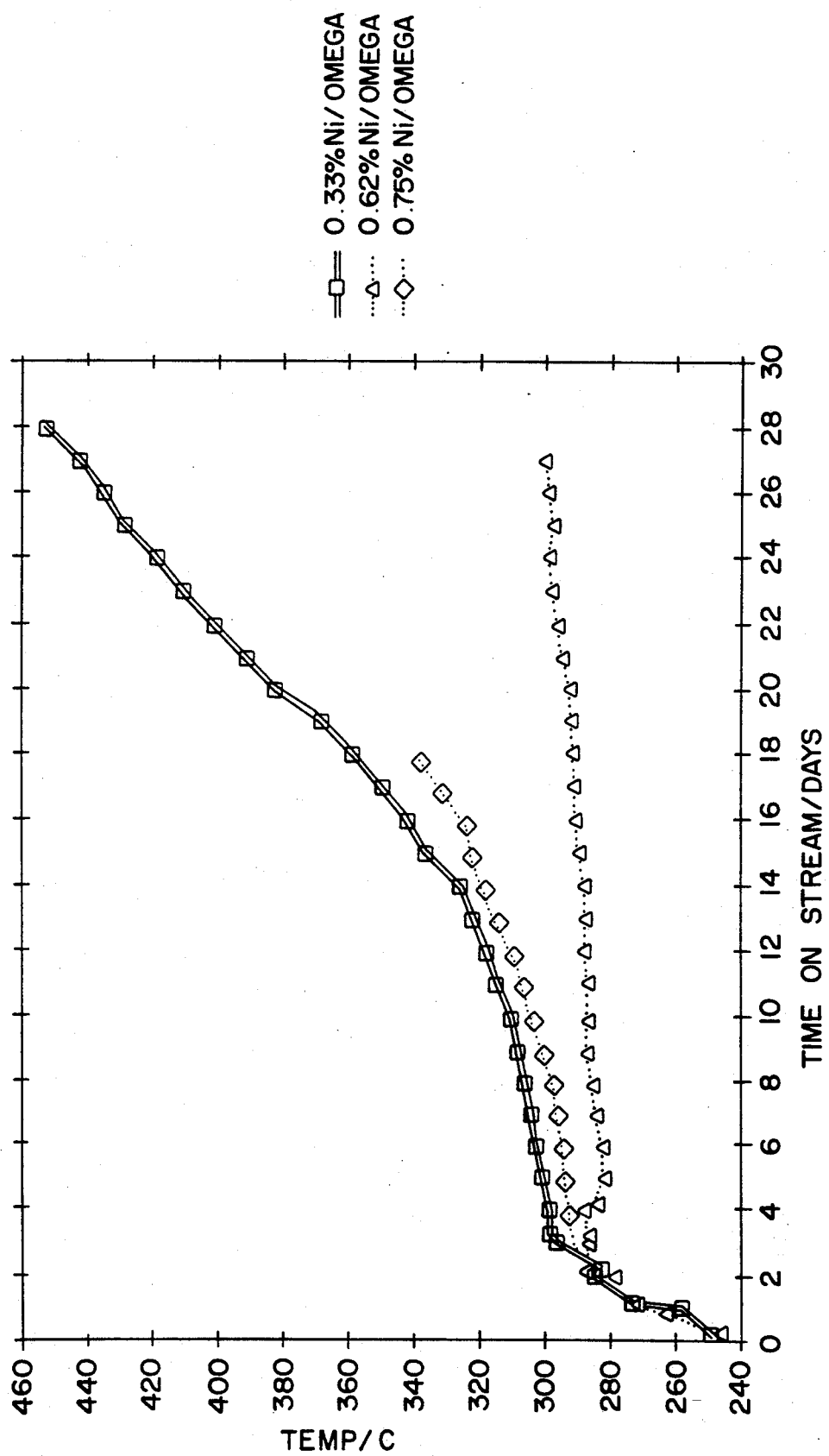
FIG. 1 graphically illustrates the relationship between reactor temperature and time on stream for each of the three metal loaded modified omega zeolite catalyst samples studied.
Figure 2:
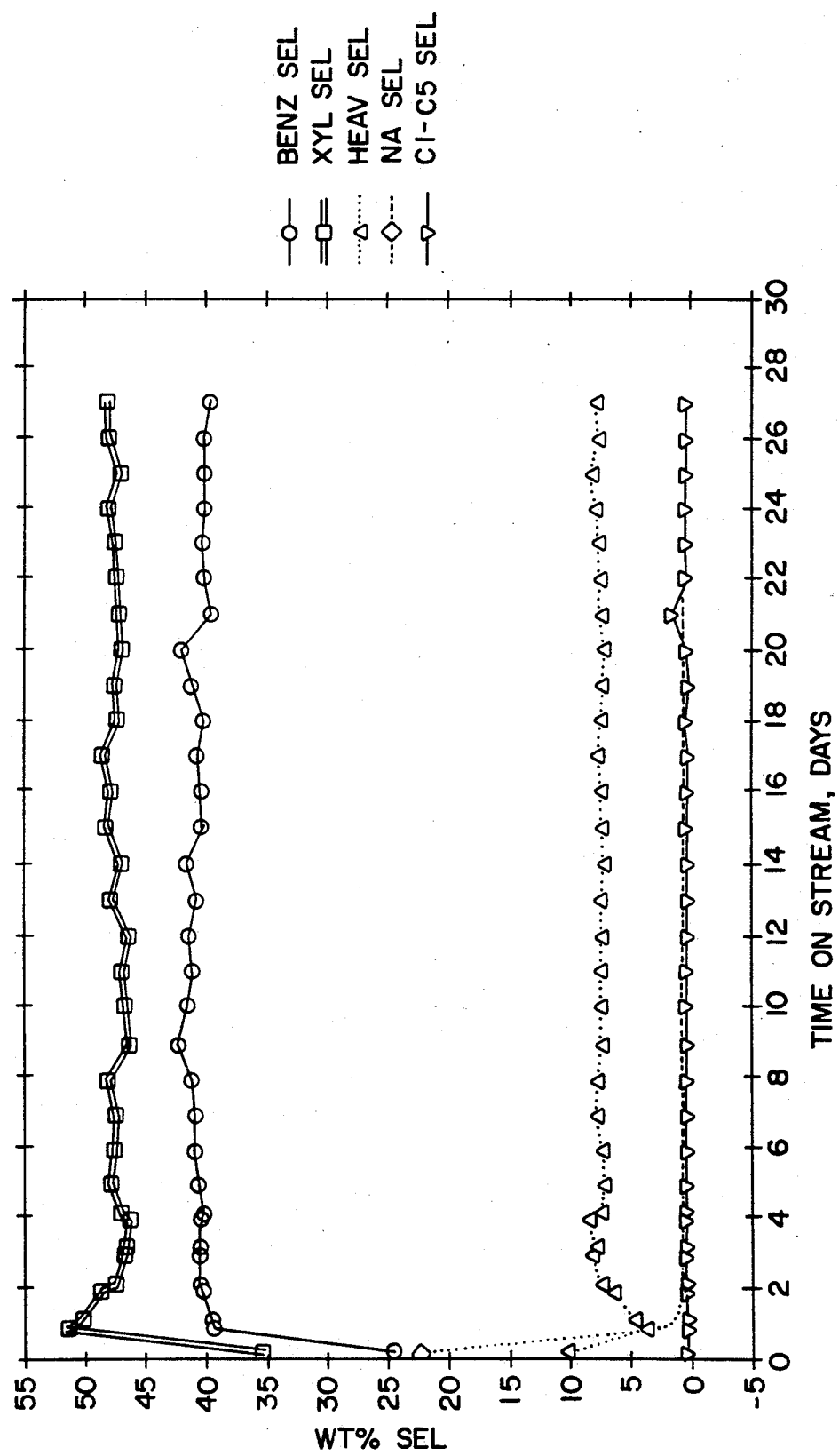
FIG. 2 graphically depicts the product selectivity of the most preferred metal loaded modified omega zeolite catalyst when employed in the disproportionation of toluene and as a function of time on stream.

The present invention relates to a stable, highly active and selective modified omega zeolite, and its preparation and use in alkylaromatic disproportionation. The preferred catalyst comprises a metal-promoted, omega zeolite composition which is particularly useful in the transalkylation of alkylaromatic compounds. The invention is particularly applicable to the transalkylation of toluene under relatively low reaction temperature producing desirably stable concentrations of benzene and xylene(s) and near equilibrium conversion of the alkylaromatic starting material. The metal-promoted omega zeolite of the present invention is prepared by the modification of the crystalline omega zeolite as synthesized. The basic procedure for the preparation of crystalline omega zeolite, which is identified by its characteristic x-ray diffraction pattern, is disclosed in U.S.

Pat. No. 4,241,036 to Flanigen, et. al. Additionally, other references such as U.S. Pat. No. 4,724,067 to Raatz, et. al. and the earlier referenced JCS article by Weeks, et. al. discuss crystalline omega zeolite compositions. The entire disclosures of each of these references are incorporated herein by reference.

Prior to modification, crystallinity of the parent omega zeolite is confirmed by way of x-ray diffraction analysis. Thereafter, the preferred omega zeolite composition which exhibits a silica to alumina molar ratio of 25:1 to 150:1 undergoes treatment as herein described.

Using standard techniques, the as synthesized zeolite omega composition is initially subjected to an ion exchange medium such as an aqueous solution of an inorganic ammonium salt, e.g. ammonium nitrate, in a relative omega-zeolite-to-ammonium-nitrate weight percentage relationship in excess of 1:2. Following this initial ion exchange, the omega zeolite is calcined at a maximum temperature of about 570° C. for a period of two or more hours. This calcination procedure is designed to burn away the organic template contained within the framework of the omega zeolite as synthesized. After calcination, the omega zeolite is subjected to two subsequent and successive ion exchange treatments each of which is performed in the same manner as described above. Following the third ion exchange, the omega zeolite is steamed, using standard techniques, at a desirable temperature within the range of 600°-770° C. and, more preferably, within the range of 690°-730° C. The omega zeolite composition next undergoes two final and successive ion exchange treatments each of which differs from the earlier exchanges in that proton ions are exchanged under acidic conditions. The introduction of an oxidizing agent such as nitric acid into the ion exchange medium assists in creating a solution of an acidic character. The surface area of steamed omega after the two successive proton ion-exchanges under acidic conditions increases from about 85 m²/g to about 555 m²/g. Additionally, the molar ratio of $SiO_2/Al_2O_3$ of the omega zeolite increases from about 7:1 to about 38:1. Following the second proton ion exchange, the omega zeolite composition is mixed with a binder such as pure alumina in the presence of nitric acid and then pelletized by any suitable technique such as extrusion. The resulting pellets are then calcined at a maximum temperature of 530° C. At this point in the modification, the omega zeolite composition is in its active hydrogen (H) form and exhibits an ammonium content of less than 0.005 wt. %. The next treatment of the omega zeolite composition involves its being loaded with a metallic hydrogenation agent such as any of the Group VIII metals and, more preferably, nickel. Employing standard techniques, the modified omega zeolite composition of the present invention is impregnated with a desirable amount of nickel or other Group VIII metal as a final modification treatment.

In a comparison study conducted over a period of twenty seven (27) days, three distinct metal-promoted, modified omega zeolite catalyst (distinguishable only based upon their weight percentage of nickel) were utilized in toluene disproportionation reactions yielding benzene and xylene(s). In this work, an omega zeolite parent compound steamed at approximately 700° C. was used. Preparation of the steamed omega composition was performed in accordance with the procedure as earlier described and as summarized in Table 1.

TABLE 1

Summary of omega zeolite modification steps together with comparative results of elemental analysis respecting Si/Al molar ratio, surface area and pore volume for each of the three omega zeolite compositions studied.

| Step # | Description of Treatment | $SiO_2/Al_2O_3$ Molar Ratio | Surface Area, $m^2/g$ | Pore Volume, ml/g |
|---|---|---|---|---|
| 0 | As synthesized with template | 6.6 | 83.2 | 0.0110 |
| 1 | 1st ammonium ion-exchange and calcined at 570° C. | | | |
| 2 | 2nd ammonium ion-exchange | | 69.1 | 0.0054 |
| 3 | 3rd ammonium ion-exchange | | 75.1 | N/A |
| 4 | Steamed at 700° C. | 7.0 | 123.2 | 0.0221 |
| 5 | 1st proton ion-exchange under acidic conditions | 14.5 | 430.6 | 0.1229 |
| 6 | 2nd proton ion-exchange under acidic conditions | 38.0 | 555.8 | 0.1535 |
| 7 | Extruded with 20% alumina binder and calcined at 530° C. | | 452.9 | |
| 8 | 0.33 wt % Ni impregnated on extrudate | 6.9 | 431.6 | 0.0992 |
| 9 | 0.62 wt % Ni impregnated on extrudate | 6.6 | 427.0 | 0.0977 |
| 10 | 0.75 wt % Ni impregnated on extrudate | 6.6 | 421.0 | 0.0959 |

The steamed omega which was subsequently proton ion-exchanged was extruded with approximately 20% pure alumina binder and was calcined at approximately 530° C. A dehydrogenating/hydrogenating metal, such as nickel, was then incorporated into the material in weight percentage quantities within the range of about 0.3 to 0.8, by utilizing a conventional impregnation technique with a nickel nitrate [$Ni(NO_3)_2$] solution. At study commencement, an established volume of the catalyst (i.e. 15 ml.) was loaded into the laboratory reactor. The reactor was then closed and pressure-tested at 1000 psi prior to sandbath introduction. Once loaded into the fluidized beds and attached to the system, the catalyst was dried by heating under hydrogen flow (0.4 L/min.) at 175°–200° C. which condition was maintained overnight. The reactor temperature was next raised to 250° C. and held. Pressure was adjusted to and maintained at a value of about 600 psig. The feed containing substantially pure (>99.6%) toluene was then introduced at a desired rate to provide a LHSV=~2. Hydrogen gas supplied as cofeed was adjusted to provide a hydrogen-to-toluene feed ratio of about 3.5:1 to 4.5:1. The reactor temperature was raised in step-wise increments of about 10°–15° C. until the conversion of toluene was obtained at a level of 46%–48%. Both liquid and gas samples were withdrawn during each collection and analyzed to calculate activity and product selectivity. Toluene conversion within the defined range was maintained by increasing reactor temperature, which increase, although small, was required due to catalyst deactivation. As revealed by Table 2, however, in which the performance of Applicant's most preferred embodiment is profiled, the rate of catalytic deactivation for the modified omega catalyst containing about 0.6 weight percent nickel was measured at a stable 0.6° C./day.

TABLE 2

Temperature, conversion and product selectivity of toluene disproportionation on Ni(0.62%)/Omega catalyst.

| Run day # | Temp/°C. | % Tol Conv | % Product Selectivity ||||| 
|---|---|---|---|---|---|---|---|
|  |  |  | Nonarom | Benzene | Xylenes | Heavies | C1–C5 Gases |
| 0.2 | 246.8 | 13.63 | 22.47 | 24.62 | 35.50 | 10.36 | 0.31 |
| 1.0 | 272.3 | 35.50 | 1.22 | 39.54 | 50.25 | 4.68 | 0.36 |
| 2.0 | 287.8 | 47.78 | 1.10 | 40.47 | 47.48 | 7.48 | 0.58 |
| 3.0 | 286.8 | 50.07 | 0.96 | 40.55 | 46.55 | 7.94 | 0.53 |
| 4.0 | 284.8 | 49.06 | 0.83 | 40.23 | 47.03 | 7.47 | 0.53 |
| 5.0 | 282.5 | 47.74 | 0.80 | 40.68 | 47.87 | 7.19 | 0.46 |
| 6.0 | 282.8 | 47.57 | 0.82 | 41.04 | 47.55 | 7.38 | 0.42 |
| 7.0 | 285.0 | 48.69 | 0.85 | 40.91 | 47.42 | 7.83 | 0.49 |
| 8.0 | 285.8 | 48.00 | 0.84 | 41.19 | 48.17 | 7.78 | 0.46 |
| 9.0 | 287.6 | 48.55 | 0.88 | 42.38 | 46.34 | 7.47 | 0.44 |
| 10.0 | 287.5 | 48.40 | 0.81 | 41.52 | 46.77 | 7.50 | 0.50 |
| 11.0 | 287.5 | 48.69 | 0.78 | 41.14 | 46.98 | 7.50 | 0.50 |
| 12.0 | 288.5 | 48.78 | 0.78 | 41.49 | 46.40 | 7.37 | 0.49 |
| 13.0 | 288.1 | 47.88 | 0.70 | 40.71 | 47.93 | 7.48 | 0.36 |
| 14.0 | 288.5 | 47.80 | 0.70 | 41.64 | 47.00 | 7.20 | 0.40 |
| 15.0 | 290.0 | 47.57 | 0.66 | 40.33 | 48.26 | 7.45 | 0.46 |
| 16.0 | 291.5 | 47.69 | 0.66 | 40.38 | 47.88 | 7.44 | 0.46 |
| 17.0 | 291.5 | 47.56 | 0.66 | 40.73 | 48.54 | 7.66 | 0.39 |
| 18.0 | 292.8 | 48.22 | 0.66 | 41.25 | 47.59 | 7.34 | 0.56 |
| 19.0 | 292.8 | 47.43 | 0.66 | 41.97 | 46.99 | 7.21 | 0.48 |
| 20.0 | 293.2 | 47.35 | 0.69 | 41.97 | 46.99 | 7.21 | 0.48 |
| 21.0 | 295.5 | 48.08 | 0.60 | 41.54 | 47.13 | 7.53 | 0.53 |
| 22.0 | 296.8 | 48.09 | 0.62 | 40.14 | 47.34 | 7.63 | 0.50 |
| 23.0 | 298.6 | 47.99 | 0.61 | 40.28 | 47.49 | 7.69 | 0.54 |
| 24.0 | 299.6 | 47.89 | 0.59 | 40.05 | 48.04 | 7.88 | 0.52 |
| 25.0 | 298.1 | 47.62 | 0.61 | 40.07 | 47.09 | 8.24 | 0.53 |
| 26.0 | 299.5 | 47.31 | 0.56 | 40.16 | 48.05 | 7.65 | 0.51 |
| 27.0 | 300.8 | 47.69 | 0.56 | 40.17 | 48.08 | 7.85 | 0.54 |

Table 3 provides a summary of the most salient performance characteristics respecting each of the three catalysts studied and includes a corresponding start of run temperature for each which is defined as the temperature at which the catalyst gives 46–48% alkylaromatic conversion at zero time on stream.

TABLE 3

Corresponding start of run temperatures and product distribution breakdown for each of the three omega zeolite catalysts studied.

| Catalyst | SOR/°C. | % Product Selectivity ||||
|---|---|---|---|---|---|
|  |  | Benzene | Xylenes | Non-aromatics | Heavies |
| 0.33% Ni/Omega | 293 | 40 | 47 | 0.5 | 7.5 |
| 0.62% Ni/Omega | 280 | 40 | 47 | 0.5 | 7.5 |
| 0.75% Ni/Omega | 289 | 40 | 47 | 0.5 | 7.5 |

We claim:

1. In a transalkylation process for the disproportionation of a toluene containing feedstock over a steam modified and metal-promoted omega zeolite catalyst to produce benzene and xylene(s), the steps comprising:
   (a) passing a cofeed of hydrogen gas and substantially pure toluene into a reaction zone and contacting it with a steam-modified and nickel-loaded omega zeolite catalyst, the catalyst having a silica to alumina molar ratio in the range of about 25:1 to 150:1, the feedstock being supplied to the reaction zone at a rate sufficient to provide a toluene LHSV of about 2;
   (b) conducting the disporportionation reaction within the reaction zone at a temperature within the range of about 250°–480° C. and at a pressure of at least 600 psig; and
   (c) withdrawing the disproportionation product containing benzene and xylene(s) from the reaction zone.

2. The process according to claim 1 wherein the reaction zone is operated at a temperature of about 250°–320° C.

3. The process according to claim 1 wherein the reaction zone is operated at a temperature of about 280° C.

4. The process according to claim 1, wherein the toluene conversion level is greater than 46% and the conversion level is maintained by adjusting the reactor temperature.

5. The process according to claim 1, wherein the toluene conversion level is about 48% and the conversion level is maintained by adjusting the reactor temperature.

6. The process according to claim 1, wherein the omega zeolite catalyst preferably exhibits a silica to alumina molar ratio of about 30:1 to 50:1.

7. The process according to claim 1, wherein the omega zeolite catalyst most preferably exhibits a silica to alumina molar ratio of about 35:1 to 40:1.

8. The process according to claim 1 wherein the metal-promoted omega zeolite catalyst contains an amount of nickel within the range 0.3–0.8 weight percent.

9. The process according to claim 1 wherein the metal-promoted omega zeolite catalyst contains an amount of nickel within the range 0.45–0.7 weight percent.

10. The process according to claim 1 wherein the metal-promoted omega zeolite catalyst contains an amount of nickel which is about 0.6 weight percent.

11. The process according to claim 1 wherein the hydrogen gas is cofed with the toluene in a weight percentage concentration of about 3.5:1 to 4.5:1.

12. The process according to claim 1, wherein the level of (liquid) non-aromatic by-product compounds in the disproportionation product decreases sharply with time on stream and shows a stable value of less than 1 wt. % of the disproportionation product.

13. The process according to claim 1, wherein the level of benzene product comprises a stable weight percentage value of about 40–41% of the disproportionation product.

14. The process according to claim 1, wherein the rate of catalytic deactivation, as measured by change in reactor temperature per day in order to maintain about 48% toluene conversion, is less than 1° C. per day.

* * * * *